(12) United States Patent
Broad

(10) Patent No.: US 10,821,474 B2
(45) Date of Patent: Nov. 3, 2020

(54) SYSTEMS AND METHODS FOR ULTRASOUND PULSE GENERATION USING GALLIUM NITRIDE FIELD EFFECT TRANSISTORS

(71) Applicant: EchoNous, Inc., Redmond, WA (US)

(72) Inventor: Ronald W. Broad, Arlington, WA (US)

(73) Assignee: EchoNous, Inc., Redmond, WA (US)

( * ) Notice: Subject to any disclaimer, the term of this patent is extended or adjusted under 35 U.S.C. 154(b) by 530 days.

(21) Appl. No.: 15/592,655

(22) Filed: May 11, 2017

(65) Prior Publication Data

US 2017/0326588 A1 Nov. 16, 2017

Related U.S. Application Data

(60) Provisional application No. 62/334,683, filed on May 11, 2016.

(51) Int. Cl.
*B06B 1/06* (2006.01)
*B06B 1/02* (2006.01)
*A61B 8/00* (2006.01)

(52) U.S. Cl.
CPC .......... *B06B 1/0215* (2013.01); *A61B 8/4444* (2013.01); *A61B 8/54* (2013.01); *B06B 1/0622* (2013.01); *A61B 8/4488* (2013.01); *A61B 8/4494* (2013.01)

(58) Field of Classification Search
CPC ....... B06B 1/0622; B06B 1/06; B06B 1/0603; B06B 1/0607
USPC ........................................ 310/322, 334, 335
See application file for complete search history.

(56) References Cited

U.S. PATENT DOCUMENTS

| | | | |
|---|---|---|---|
| 5,394,047 A | 2/1995 | Scharlack et al. | |
| 5,900,690 A | 5/1999 | Gipson et al. | |
| 2006/0103267 A1* | 5/2006 | Lupien | B06B 1/0625 310/334 |
| 2006/0149169 A1 | 7/2006 | Nunomura et al. | |
| 2008/0287791 A1 | 11/2008 | Orszulak et al. | |
| 2011/0060225 A1* | 3/2011 | Cogan | B06B 1/0207 600/459 |
| 2011/0233559 A1* | 9/2011 | Ishikura | H01L 21/823481 257/76 |
| 2013/0072921 A1 | 3/2013 | Behnke, II et al. | |
| 2013/0258803 A1* | 10/2013 | Nakamura | B06B 1/0622 367/7 |

(Continued)

*Primary Examiner* — Derek J Rosenau
(74) *Attorney, Agent, or Firm* — Seed Intellectual Property Law Group LLP

(57) ABSTRACT

Circuits, devices and methods generating an ultrasound pulse are provided herein. An ultrasound probe includes an array of transducer elements configured to transmit an ultrasound signal toward a target structure in a region of interest, and an array of pulse generators for driving a respective transducer element. Each of the pulse generators are coupled to a respective transducer element and include a driver circuit configured to receive a control signal and to output a driving signal, a switching element coupled to the driver circuit, and a resonant circuit coupled to the switching element and the respective transducer element, wherein the resonant circuit is configured to provide a transmit pulse to the respective transducer element based on the driving signal. The switching element may comprise a gallium nitride field effect transistor (GaN FET).

20 Claims, 6 Drawing Sheets

(56) References Cited

U.S. PATENT DOCUMENTS

2013/0310689 A1 11/2013 Nishigaki
2014/0307521 A1 10/2014 Kameishi et al.

\* cited by examiner

SYSTEMS AND METHODS FOR ULTRASOUND PULSE GENERATION USING GALLIUM NITRIDE FIELD EFFECT TRANSISTORS

BACKGROUND

Technical Field

The present application pertains to ultrasound systems, and more particularly to ultrasound probes including pulser circuits for generating and providing a transmit pulse to a respective transducer element.

Description of the Related Art

Ultrasound imaging is useful as an imaging modality in a number of environments. For example, in the field of healthcare, internal structures of a patient's body may be imaged before, during or after a therapeutic intervention. A healthcare professional may hold a portable ultrasound probe, or transducer, in proximity to the patient and move the transducer as appropriate to visualize one or more target structures in a region of interest in the patient. A transducer may be placed on the surface of the body or, in some procedures, a transducer is inserted inside the patient's body. The healthcare professional coordinates the movement of the transducer so as to obtain a desired representation on a screen, such as a two-dimensional cross-section of a three-dimensional volume.

Ultrasound may also be used to measure functional aspects of a patient, such as organ movement and blood flow in the patient. Doppler measurements, for example, are effective in measuring the direction and speed of movement of a structure, such as a heart valve or blood cells flowing in a vessel, relative to the transducer. Doppler echocardiography is widely used for evaluating the cardiocirculatory system of patients with known or suspected cardiovascular disease.

For many years, ultrasound imaging was effectively confined to large equipment operating in a hospital environment. Recent technological advances, however, have produced smaller ultrasound systems that increasingly are deployed in frontline point-of-care environments, e.g., doctors' offices. Nevertheless, smaller ultrasound systems typically lack the power, thermal management, and processing capabilities of larger systems. This generally results in limited runtime of the ultrasound imaging components, lower image resolution, and fewer features or modes of operation.

Conventional ultrasound devices typically employ double-diffused metal-oxide-semiconductor (DMOS) type field effect transistors (FETs) in the ultrasound pulser circuit, which is usually located outside of the ultrasound probe (e.g., within an ultrasound equipment rack or computer that is connected to the ultrasound probe via one or more cables). These transistors typically require significant gate drive current to achieve the high edge rates needed for generating high bandwidth transmit pulses.

When designing an ultrasound pulser circuit to be located within the ultrasound probe, however, certain issues may exist which are not of particular importance in conventional systems that have the pulser circuits located in large equipment connected to the ultrasound probe by one or more cables. For example, in an ultrasound pulser circuit within the ultrasound probe, power losses become significantly more important (as, for example, heat dissipated in the probe can be undesirably transferred to a patient or to a user operating the probe). Further, for ultrasound pulser circuits located within a probe, the capacitance of the cable that otherwise connects the probe to larger equipment is no longer present. This makes the conventional, large DMOS type devices less attractive in such a system. Benefits may be experienced, therefore, in addressing one or more of these issues in order to permit placement of the pulser circuit within the ultrasound probe of a portable or ultraportable ultrasound system.

BRIEF SUMMARY

The present application, in part, addresses a desire for smaller ultrasound systems, having greater portability, lower cost, and ease of use for different modes of ultrasound imaging, while at the same time providing high quality measurements.

In addition, recent developments in high frequency gallium nitride field effect transistor (GaN FET) technology have created devices with lower input capacitances and good high voltage characteristics. According to one aspect of the present invention, these devices may be utilized in ultrasound pulser designs in accordance with embodiments provided herein.

In at least one embodiment, an ultrasound probe is provided that includes an array of transducer elements and an array of pulse generators. The array of transducer elements is configured to transmit an ultrasound signal toward a target structure in a region of interest. Each of the pulse generators in the array of pulse generators is coupled to a respective transducer element. Each of the pulse generators includes a driver circuit configured to receive a control signal and to output a driving signal, a switching element coupled to the driver circuit, and a resonant circuit coupled to the switching element and the respective transducer element. The resonant circuit is configured to provide a transmit pulse to the respective transducer element based on the driving signal.

In another embodiment, an ultrasound device is provided that includes an ultrasound probe and a handheld computing device coupled to the ultrasound probe. The ultrasound probe includes an array of transducer elements configured to transmit an ultrasound signal toward a target structure in a region of interest, and an array of pulse generators. Each of the pulse generators in the array of pulse generators is coupled to a respective transducer element and includes a driver circuit configured to receive a control signal and to output a driving signal, a switching element coupled to the driver circuit, and a resonant circuit coupled to the switching element and the respective transducer element. The resonant circuit is configured to provide a transmit pulse to the respective transducer element based on the driving signal.

In yet another embodiment, a method for generating an ultrasound transmit pulse in an ultrasound probe is provided. The method includes resonating a resonant circuit in the ultrasound probe by turning on a gallium nitride field effect transistor (GaN FET) based on a first driving signal, and generating a first transmit pulse by turning off the GaN FET based on a second driving signal.

In still another embodiment, a method of forming an ultrasound pulse generation circuit is provided. The method includes: forming, in an ultrasound probe, a driver circuit, a switching element, an RLC resonant circuit and a transducer element; coupling the RLC resonant circuit to a power supply at a first node; coupling the RLC resonant circuit to the transducer element at a second node; and coupling a control terminal of the switching element to an output terminal of the driver circuit.

DETAILED DESCRIPTION

A handheld ultrasound probe may include an array of transducer elements and an array of pulse generators located within the probe. Each of the transducer elements is coupled to a respective pulse generator, which generates transmit pulses for driving the associated transducer element. The pulse generators (or "pulsers") are driven by control signals provided from a controller circuit, which may be located within the probe or, alternatively, in a computer device which is operably coupled to the probe, e.g., via a cable. Each pulser may include a GaN FET switching element that is controlled (e.g., turned on and off) based on the control signals, and which causes a resonant portion of the pulser to resonate. By turning off the GaN FET switching element, while the pulser is resonating, a transmit pulse is generated and provided to the associated transducer element, which accordingly transmits an ultrasound signal based on the transmit pulse.

Figure 1:
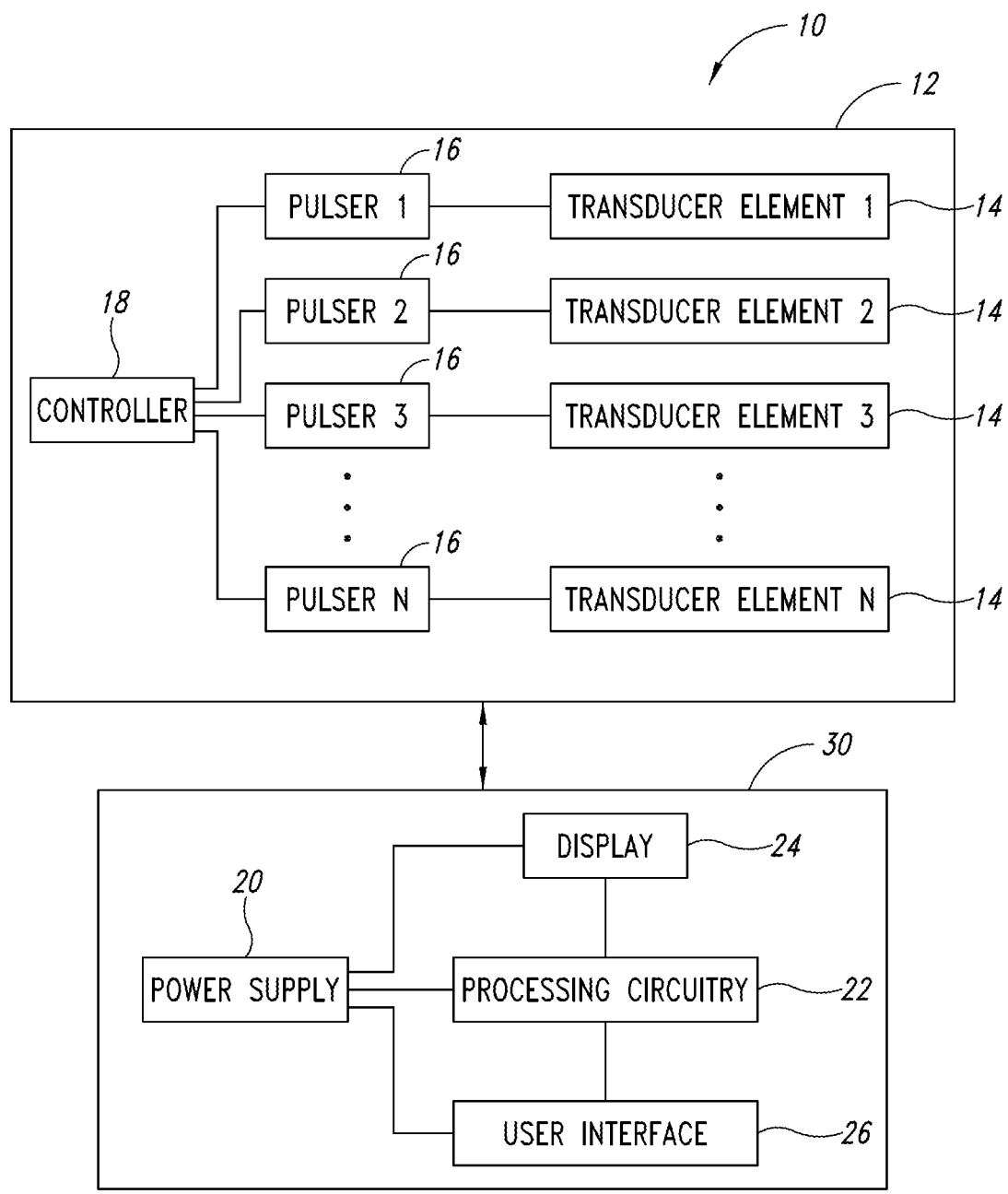
FIG. 1 is a block diagram illustrating an ultrasound system, in accordance with one or more embodiments of the present disclosure.

FIG. 1 is a block diagram illustrating an ultrasound system 10, in accordance with one or more embodiments of the present disclosure. The ultrasound system 10 includes a handheld ultrasound probe 12 and a computing device 30. The ultrasound probe 12 is electrically coupled to the computing device 30 by any wired or wireless electrical connections. The ultrasound system 10 may be a portable ultrasound system, i.e., the probe 12 may be connected to a portable computing device 30, such as a tablet computer, laptop or the like.

The ultrasound probe 12 includes an array of transducer elements 14 (e.g., transducer elements 1 through N) and an array of pulse generators or pulsers 16 (e.g., pulsers 1 through N) arranged on or within a housing of the probe 12. The transducer elements 14 are configured to transmit an ultrasound signal toward a target structure in a region of interest. The transducer elements 14 may further be configured to receive echo signals returning from the target structure in response to transmission of the ultrasound signal. In various embodiments, the transducer elements 14 may be arranged as elements of a phased array transducer. Suitable phased array transducers are known in the field of ultrasound technology.

Each transducer element 14 is coupled to an associated pulser 16, which drives the transmission of an ultrasound signal from the associated transducer element 14 toward a target structure or functional aspect in a region of interest (e.g., organs, tissue, blood vessels, heart valve or any other structure or function of interest in a patient).

The array of transducer elements 14 is operable to transmit an ultrasound beam to the target structure and to receive echo signals reflected from the target structure. The received signals contain information about the target structure and may be processed (e.g., by processing circuitry 22 in the computer device 30) to form an ultrasound image.

The ultrasound system 10 further includes a controller circuit (or "controller") 18, which may be located within the probe 12 (e.g., within the housing of the probe 12) or, alternatively, may be located within the computing device 30. In one or more embodiments, the controller 18 may be, or may include, an application-specific integrated circuit (ASIC) or a field programmable gate array (FPGA). The controller 18 is coupled to the pulsers 16 and supplies control signals for driving the pulsers 16, which in turn drive the transmission of ultrasound signals from the respectively associated transducer elements 14.

The controller 18 may thus control the generation and timing of transmit pulses by the pulsers 16 so as to cause the transducer elements 14 to collectively form a desired ultrasound transmission pattern or beam. The controller 18 may include an oscillator or clock, and may thus cause the pulsers 16 to generate the transmit pulses in synchronization with the oscillator or clock. The controller 18 may be further operable to control the transmission amplitude or transmission power of the transmit pulses, for example, by utilizing pulse width modulation (PWM) to form the control signals that drive the pulsers 16.

The ultrasound system 10 further includes a power supply 20, which may be located within the probe 12 (e.g., within the housing of the probe 12) or within the computing device 30. The power supply 20 is coupled to the pulsers 16 and supplies electrical power to the pulsers 16 for generating pulse signals to drive the respective associated transducer elements 14. The power supply 20 may further be coupled to the controller 18. In particular, the power supply 20 provides power for generating electrical signals by the pulsers 16, with stepped-up voltage as needed, that cause the transducer elements 14 to transmit an ultrasound signal. The power supply 20 may further be electrically coupled to any other component parts of the ultrasound device 10. Such component parts may include, for example, the computer device 30, including the processing circuitry 22, the display 24 and/or the user interface 26. The power supply 20 may be, for example, one or more batteries in which electrical energy is stored.

The computing device 30 includes a display 24 and a user interface 26. The display 24 may incorporate any type of display technology including, but not limited to, LED display technology. The display 24 is used to display one or more images generated from echo data obtained from the echo signals received in response to transmission of an ultrasound signal. In some embodiments, the user interface 26 may include one or more buttons, knobs, switches, and the like, capable of receiving input from a user of the ultrasound system 10. In some embodiments, the display 24 may be a touch screen that is also capable of receiving input from a user that touches the screen.

The computing device 30 may further include one or more audio speakers for generating audible representations of echo signals or other features derived from operation of the ultrasound system 10.

The ultrasound system 10 further includes processing circuitry 22, which may be included within the computer device 30 or the probe 12, or both. In various embodiments, the processing circuitry 22 includes one or more programmed processors that operate in accordance with computer-executable instructions that, in response to execution, cause the programmed processor(s) to perform various actions. For example, the processing circuitry 22 may be configured to send one or more control signals to the controller 18 to control the transmission of an ultrasound signal by the ultrasound transducers 14. The processing circuitry 22 is further coupled to the user interface 26 and the display 24, and may control a variety of operational parameters associated with the controller 18, the display 24 and the user interface 26.

In one or more embodiments, the controller 18 may be included in, or executed by, the processing circuitry 22. For example, the controller 18 may be a module executed by one or more processors included in the processing circuitry 22. In other embodiments, the controller 18 may be configured with processing circuitry separate from the main processing circuitry 22 in the computer device 30 and may operate in cooperation with the processing circuitry 22. The processing circuitry of the controller 18 may be a programmed processor, an FPGA and/or an application-specific integrated circuit (ASIC) configured to provide the pulser control functions described herein.

Figure 2:
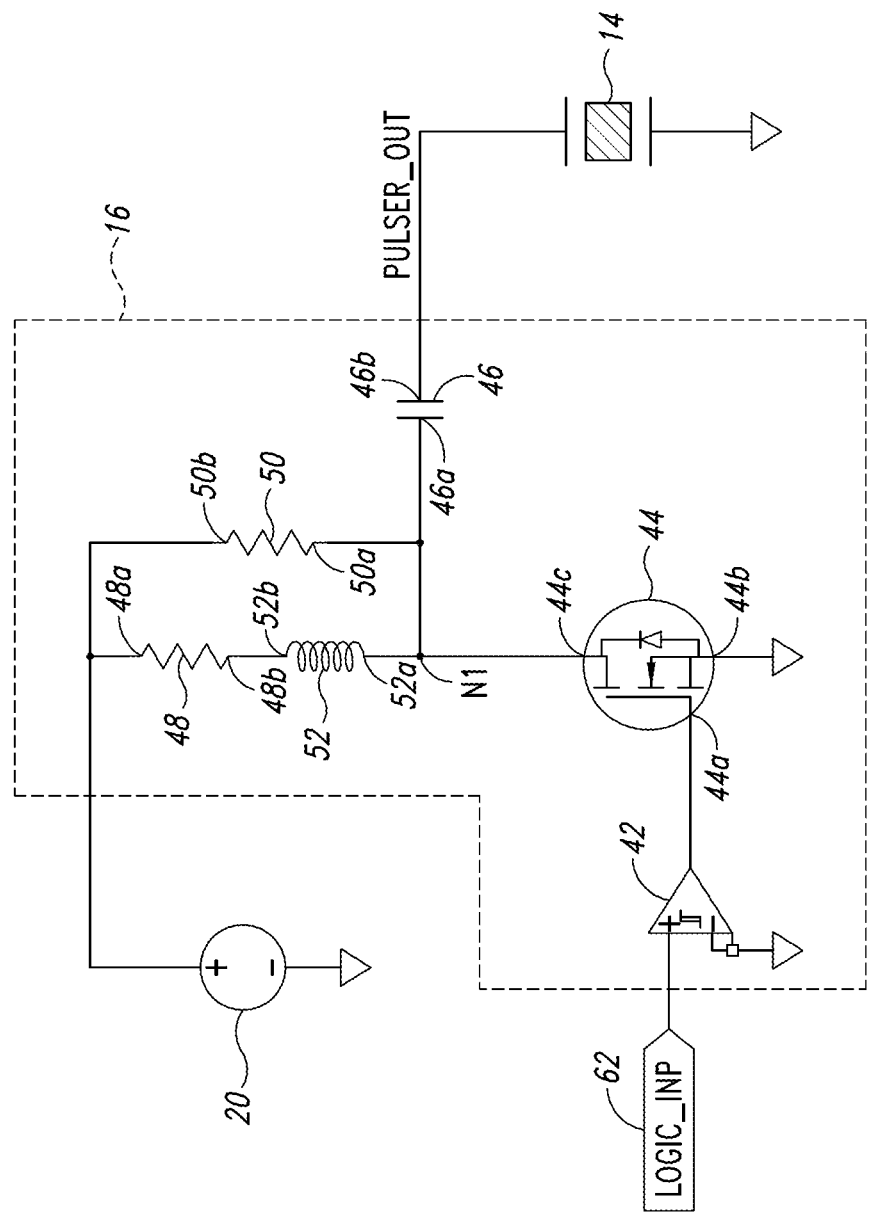
FIG. 2 is a circuit diagram illustrating an ultrasound pulser, in accordance with one or more embodiments of the present disclosure.

FIG. 2 is a circuit diagram illustrating an ultrasound pulser 16, in accordance with one or more embodiments of the present disclosure. The pulser 16 includes a driver circuit 42, a switching element 44, a capacitor 46, first and second resistors 48, 50, and an inductor 52. The pulser 16 is powered by the power supply 20. The ultrasound probe 12 may include an array of pulsers 16, with each pulser 16 within the array being coupled to a respective transducer element 14.

The driver circuit 42 is coupled to the controller 18 and receives a control signal 62 from the controller 18 for driving the pulser 16, which in turn drives the transducer element 14 to transmit an ultrasound signal. The driver circuit 42 may be, for example, a comparator with hysteresis formed of an operational amplifier with an inverting input terminal coupled to a reference voltage (such as an electrical ground, as shown in FIG. 2) and a non-inverting input terminal coupled to the controller 18 for receiving the control signal 62.

An output of the driver circuit 42 is coupled to a control terminal 44a of the switching element 44. In one or more embodiments, the switching element 44 is a gallium nitride based field effect transistor (GaN FET). In comparison to silicon-based transistors, it has been discovered that a GaN FET 44 advantageously provides several significant benefits when utilized with a resonant circuit to generate transmit pulses by the pulser 16. For example, in comparison to conventional silicon-based transistors, the GaN FET 44 has a very low on-state resistance (i.e., the resistance between the drain and source terminals is very low when the GaN FET is turned on, when which results in improved efficiency in the pulser 16), high voltage rating (which may be needed to achieve a desired power level), higher switching frequency and low gate capacitance (and thus less power is required for the driver circuit 42 to drive the control terminal 44a of the GaN FET).

As shown in FIG. 2, a first conduction terminal 44b of the switching device 44 is coupled to an electrical ground. A second conduction terminal 44c of the switching device 44 is coupled to a first terminal 52a of the inductor 52, a first terminal 50a of the second resistor 50 and a first terminal 46a of the capacitor 46 at the node N1. The first resistor 48 has a first terminal 48a coupled to the power supply 20 and a second terminal 48b coupled to a second terminal 52b of the inductor 52. The second resistor 50 has a second terminal 50b coupled to the power supply 20. The capacitor 46 is coupled to the transducer element 14 by a second terminal 46b.

In operation, the pulser 16 operates the switching element 44 (e.g., a GaN FET) as a switch to ground in order to provide a transmit pulse to the transducer element 14 for generating an ultrasound signal. When the control signal 62 from the controller 18 goes active (e.g., when the control signal 62 is a logic high) and provides a first driving signal to the switching element 44, the voltage of the first driving signal at the control terminal 44a causes the switching element 44 to conduct, and current begins to flow though the inductor 52. The ON time of the switching element 44, combined with the values of the inductor 52 and the first resistor 48, determines the amplitude of the pulse to be delivered to the transducer element 14. Accordingly, it is readily appreciated that the inductor 52 and the resistor 48 may be selected to have an inductance and a resistance value, respectively, in order to provide pulses having an amplitude as desired.

Further, the inductor 52 may be chosen to have a value of inductance such that the pulser 16, and in particular the RLC portion of the pulser 16 (e.g., the first and second resistors 48, 50, the inductor 52 and the capacitor 46), resonates at or near the natural resonance frequency of the transducer element 44. As such, the pulser 16 may provide real power to the transducer element 44 at or near its natural resonant frequency when the switching element 44 is turned off. This sequence begins the transmit pulse. The switching element 44 turns off in response to the control signal 62 being a logic low (or otherwise indicating the switching element 44 should be off) and provides a second driving signal to the switching element 44 causing the switching element 44 to turn off.

For additional cycles (e.g., to create a pulse train), the switching element 44 may again be activated in phase with the already started resonant oscillation of the RLC portion of the pulser 16. For example, the control signal 62 from the controller 18 may again go active (e.g., a logic high) and provide a third driving signal to the switching element 44, causing the switching element 44 to conduct in phase with respect to the phase of resonance in the resonant circuit. The control signal 62 from the controller 18 may then go to a logic low (or otherwise indicate the switching element 44 should be off), thereby providing a fourth driving signal that causes the switching element 44 to turn off and thus generates a second transmit pulse.

To end the burst of the pulser output, the switching element 44 may be activated (i.e., turned ON based on the control signal 62 again going to an active or logic high state) out of phase with the oscillation of resonance in the pulser circuit 16. It is readily appreciated by those skilled in the relevant technology that, by using appropriate pulse widths to drive the gate or control terminal 44a of the GaN FET switching element 44, transmit pulses of varying amplitude, bandwidth, and frequency can be generated as desired.

The second resistor 50 is used to reduce the Q factor of the resonant circuit (e.g., by dampening the oscillation of the resonant circuit) of the pulser 16, which provides for better control of the frequency response.

To choose the proper gate drive waveforms, an equivalent electrical model of a transducer element 14 was used for SPICE simulations. These simulations allow detailed measurements of the voltage and currents in the pulser circuit 16 shown in FIG. 2.

Figure 3:
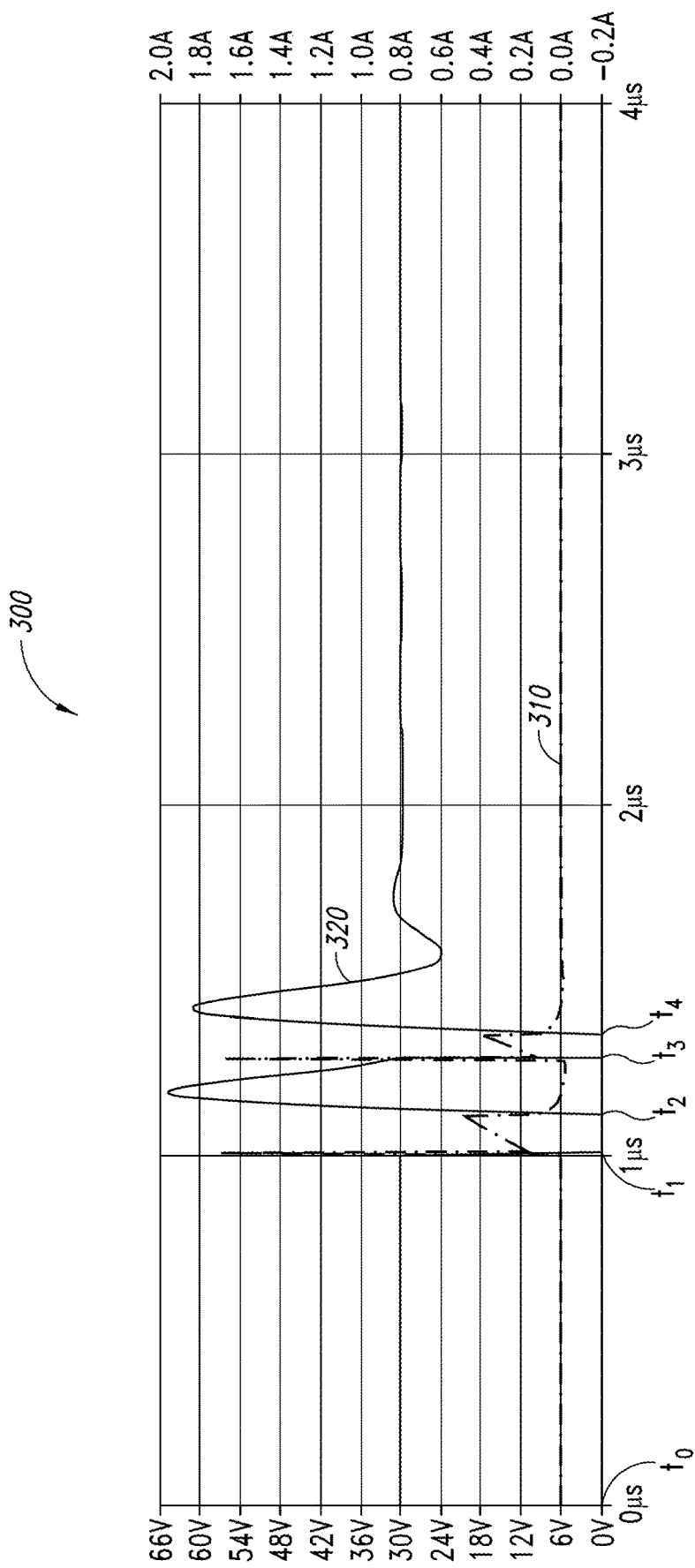
FIG. 3 is a plot illustrating current and voltage values with respect to time when utilizing a GaN FET as the switching element in the ultrasound pulser shown in FIG. 2, in accordance with one or more embodiments of the present disclosure.
Figure 4:
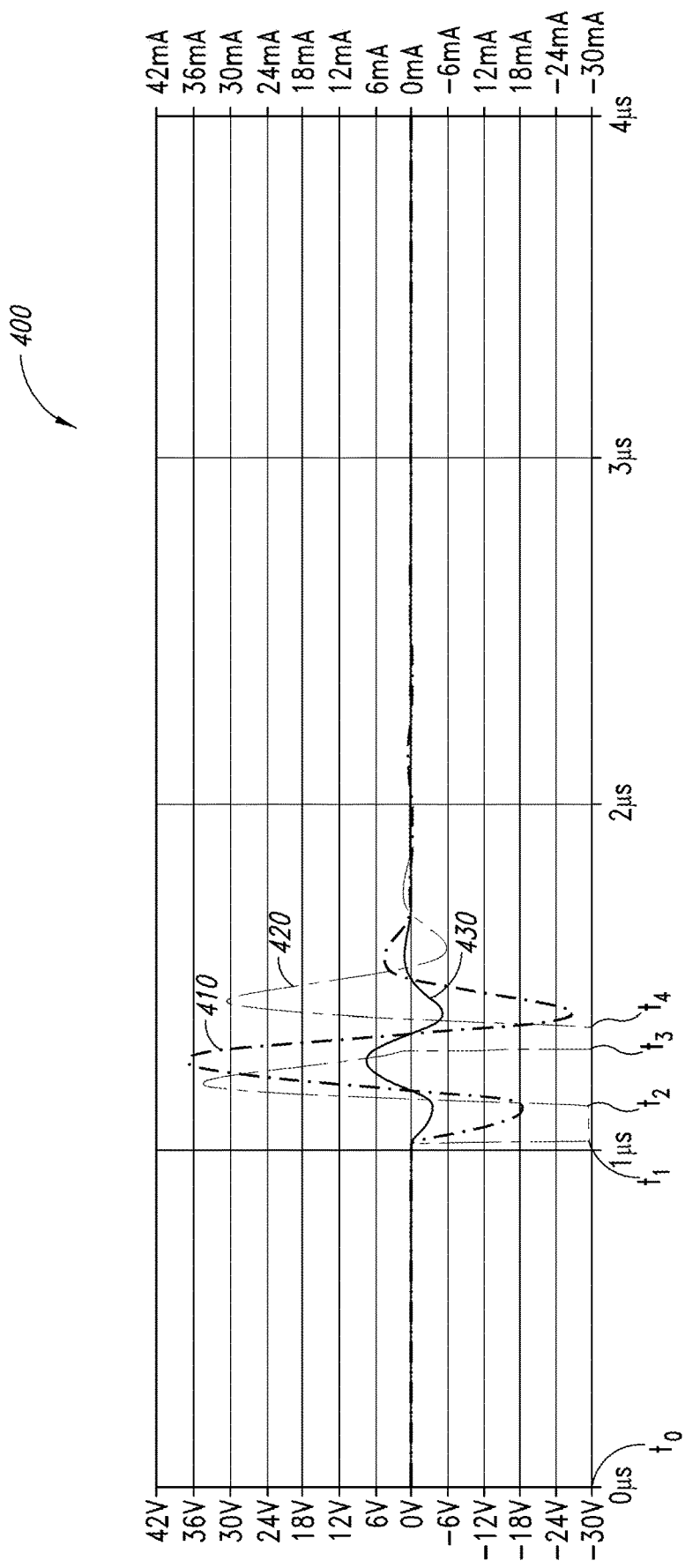
FIG. 4 is a plot illustrating the current flowing in the series resonant leg of a transducer element model, the voltage across the transducer element and the level of the acoustical wave created by the transducer element, in accordance with one or more embodiments of the present disclosure.

FIG. 3 is a plot 300 showing current and voltage values (y-axis) with respect to time (x-axis) when utilizing a GaN FET as the switching element 44 in the ultrasound pulser 16 shown in FIG. 2. The current in the GaN FET 44 is shown by reference numeral 310 and the voltage at the drain (i.e., at the second conduction terminal 44c) of the switching element 44 is shown by reference numeral 320. The voltage waveform 320 appears across the transducer element 14, after the capacitor 46 removes the DC component of the pulser output (as shown in FIG. 4).

As can be seen from FIG. 3, from time $t_0$ until time $t_1$, the switching element 44 is turned off, e.g., as the control signal 62 provided from the controller 18 to the driver circuit 42 is a logic low or otherwise indicates the switching element 44 should be off. Thus, a steady DC voltage 320 (e.g., the voltage supplied by the power supply 20) is present at the second conduction terminal 44c of the switching element 44.

At time $t_1$, the control signal 62 provided from the controller 18 indicates the switching element 44 should be on (e.g., an active state, or a logic high). The driver circuit 42 thus outputs a driving signal to the control terminal 44a to turn on the switching element 44. Accordingly, from time $t_1$ to time $t_2$, the voltage 320 at the second conduction terminal 44c of the switching element 44 goes to 0V (in this example), while the current 310 through the switching element 44 increases approximately linearly (i.e., as the capacitor 46 charges) and this current begins to flow though the inductor 52.

At time $t_2$, the control signal 62 provided from the controller 18 indicates the switching element 44 should be turned off (e.g., a logic low), and the driver circuit 42 thus turns off the switching element 44 (e.g., by turning off the driving signal from the control terminal 44a). When the switching element 44 stops conducting at time $t_2$, the voltage 320 at the second conduction terminal 44c of the switching element 44 begins to increase and the pulser circuit 16 begins to resonate.

At time $t_3$, the switching element 44 is again turned on (e.g., the control signal 62 goes high, and the driver circuit 42 turns on the switching element 44). Accordingly, from time $t_3$ to time $t_4$, the voltage 320 at the second conduction terminal 44c of the switching element 44 goes to 0V, while the current 310 through the switching element 44 increases approximately linearly and this current begins to flow though the inductor 52.

At time $t_4$, the switching element 44 is once again turned off (e.g., the control signal 62 goes low, and the driver circuit 42 turns off the switching element 44). The switching element 44 stops conducting at time $t_4$, the voltage 320 at the second conduction terminal 44c of the switching element 44 begins to increase and the pulser circuit 16 continues to resonate until the voltage 320 eventually settles to the DC voltage value (e.g., 30 volts) provided by the power supply 20. As noted above, the value of the second resistor 50 controls the Q factor of the pulser circuit 16, and thus controls the rate of dampening of the oscillating voltage waveform 320 after time $t_4$.

FIG. 4 is a plot 400 showing the current flowing in the series resonant leg of the model transducer element 14 (shown by reference numeral 410), the voltage across the transducer element 14 (shown by reference numeral 420) and the magnitude of the acoustical wave created by the transducer element 14 (shown by reference numeral 430). The timing of the plot 400 of FIG. 4 corresponds with the timing of the plot 300 of FIG. 3 (i.e., times $t_0$ to $t_4$ of FIG. 4 correspond respectively to times $t_0$ to $t_4$ of FIG. 3). As can be seen by inspection of the acoustical waveform 430, a wideband acoustical waveform has been excited in the transducer element 14.

Figure 5:
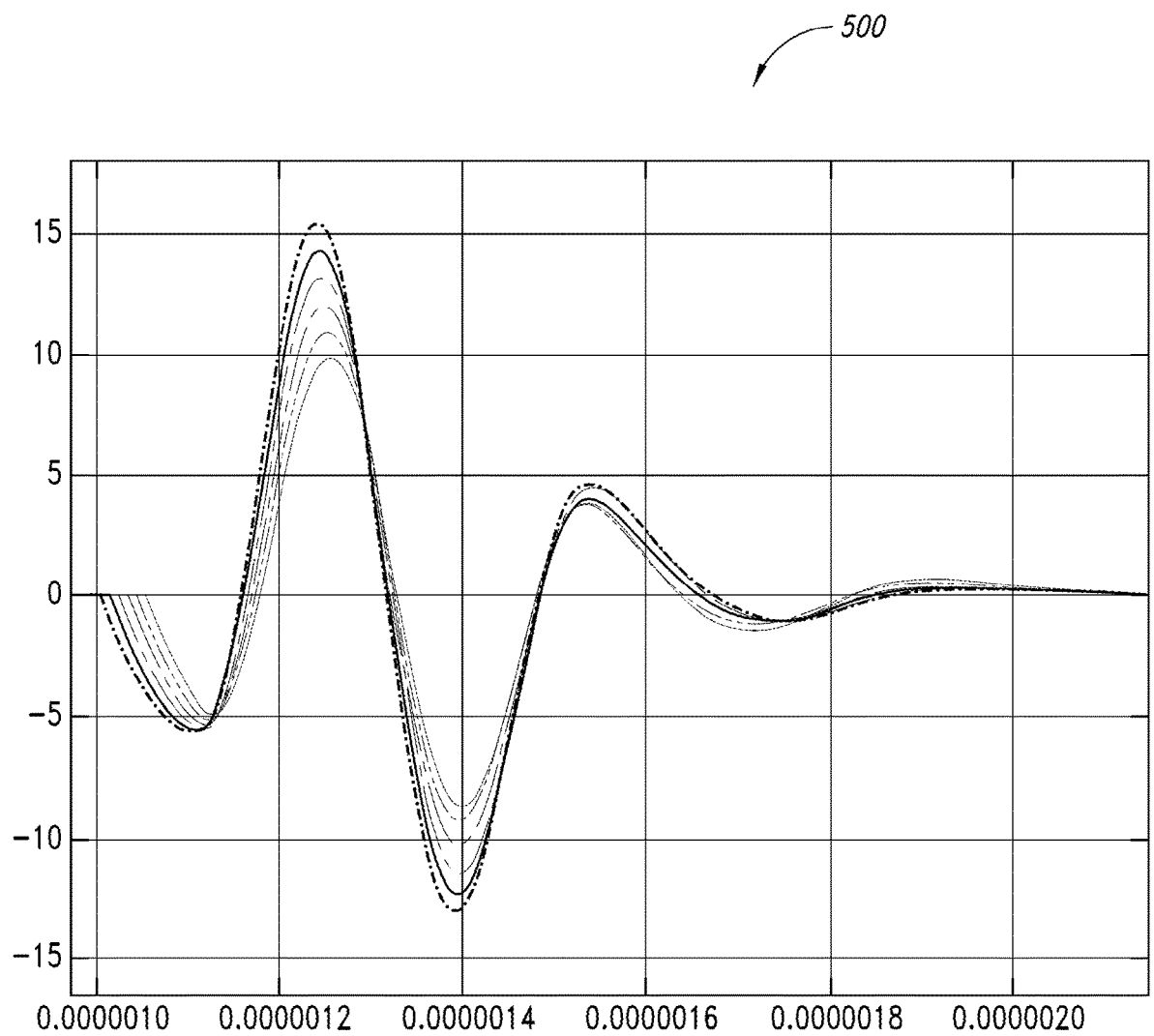
FIG. 5 is a plot illustrating acoustical waveforms generated by a transducer element in response to control signals provided to the driver circuit having varying pulse widths, in accordance with one or more embodiments of the present disclosure.

FIG. 5 is a plot 500 showing the resulting acoustical waveforms generated by the transducer element 14 in response to control signals 62 provided to the driver circuit 42 having varying pulse widths. In the simulation shown in FIG. 5, a linear step of pulse widths for the control signals 62 was used, with pulse widths ranging from 60 ns to 110 ns, with each successive control signal 62 having an increased pulse width of 10 ns.

The second pulse also steps by 10 ns from 30 ns to 70 ns. The delay between pulses provided by the control signals 62 may be tuned to maximize bandwidth while still being quantized, e.g., to 10 ns steps. By quantizing the delay between pulses, a field programmable gate array (FPGA) or an application-specific integrated circuit (ASIC) may more effectively be utilized as the controller 18 for controlling all of the pulsers 16 in the ultrasound probe 12.

As shown in FIG. 5, amplitude control of the acoustic waveform transmitted by the ultrasound transducers 14 may be achieved through controlling the pulse width of the control signals 62, as well as by controlling an amount of delay between pulses generated based on the control signals 62. By using amplitude control across the active transducer elements 14 in the transmit aperture, control of the resulting ultrasound beam width may be achieved. This may be achieved, in view of the present disclosure, without increasing the losses in the transmitter circuitry commonly seen in linear drivers, such as the class B drivers of high-end ultrasound machines.

Amplitude control can also be used to adjust the pulse magnitude for different beam types without the need for multiple high voltage power supplies or the time required to change voltage levels between beam types, as are commonly used in the conventional ultrasound pulse generation circuits.

Figure 6:
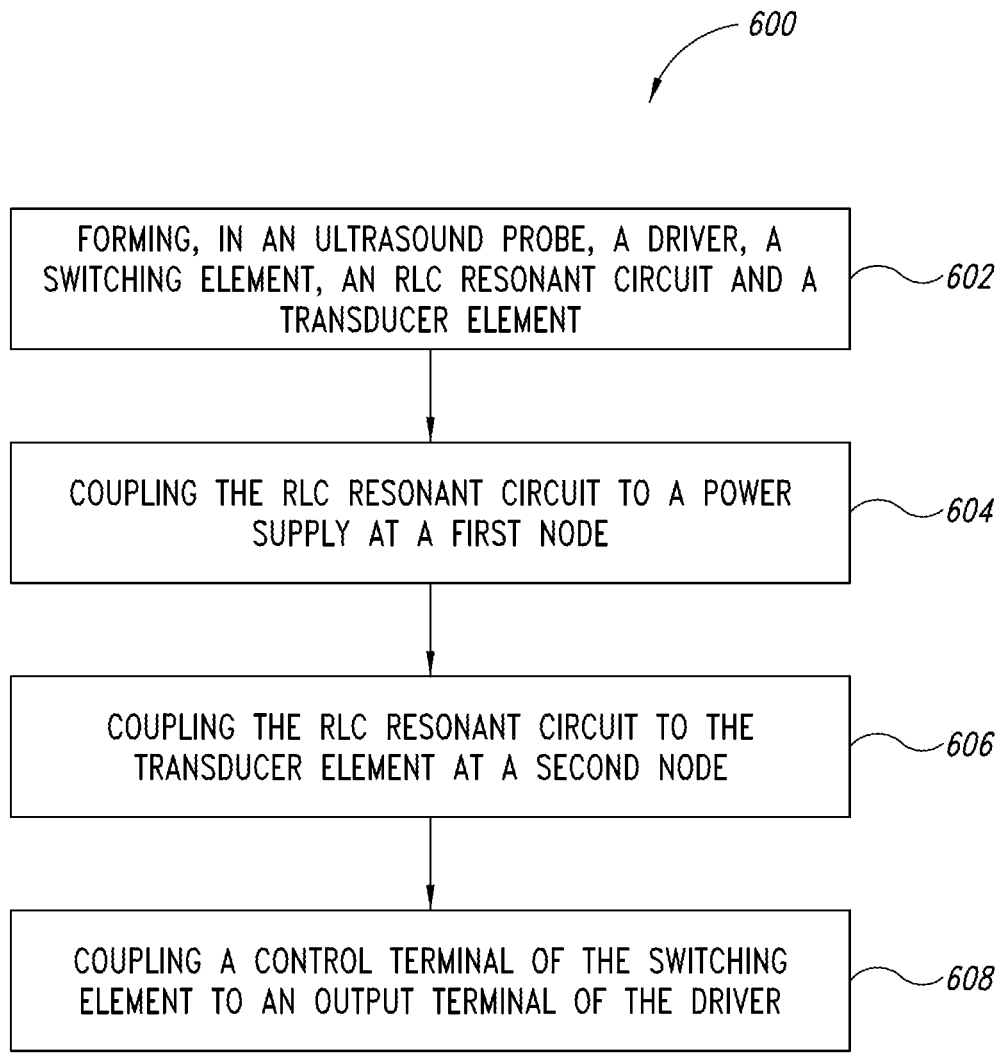
FIG. 6 is a flow diagram illustrating a method of forming an ultrasound pulse generation circuit, in accordance with one or more embodiments of the present disclosure

FIG. 6 is a flow diagram illustrating a method 600 of forming an ultrasound pulse generation circuit 16, in accordance with one or more embodiments of the present disclosure. In at least one embodiment, the method 600 includes, at block 602, forming, in an ultrasound probe 12 (e.g., within a housing of the ultrasound probe 12), a driver circuit 42, a switching element 44 (e.g., a GaN FET), an RLC resonant circuit and a transducer element 14. The RLC resonant circuit may include, for example, the first and second resistors 48, 50, the inductor 52 and the capacitor 46, as shown in FIG. 2.

At block 604, the method 600 includes coupling the RLC resonant circuit to a power supply 20 at a first node. The first node may be, for example, the shared node coupling the first and second resistors 48, 50 to the power supply 20 as shown in FIG. 2. The power supply 20 may be included in the ultrasound probe 12, or may be included, for example, in a computer device 30 that is operatively coupled to the probe 12.

At block 606, the method 600 includes coupling the RLC resonant circuit to the transducer element 14 at a second node. The second node may be, for example, the node coupling the capacitor 46 to the transducer element 14 as shown in FIG. 2.

At block 608, the method 600 includes coupling a control terminal 44*a* of the switching element 44 to an output terminal of the driver circuit 42.

The method 600 may be repeated for forming an array of pulse generation circuits 16, with each such pulse generation circuit 16 being coupled to a respective transducer element 14 in an array of transducer elements 14.

While the pulsers 16 are shown and described herein as being positioned within the handheld ultrasound probe 12, it will be readily appreciated that the pulsers 16, as well as other elements described herein (e.g., the controller 18), may be included within the ultrasound probe 12 and/or the computing device 30. For example, the ultrasound pulser 16 shown in FIG. 2 may be positioned within the computing device 30 (such as, for example, an ultrasound computing device located on an equipment rack, as in conventional ultrasound imaging systems), and electrically coupled to the transducer element 14 via one or more cables.

As may be appreciated by persons having ordinary skill in the art, aspects of the various embodiments described above can be combined to provide further embodiments. Aspects of the embodiments can also be modified, if necessary, to employ concepts of various patents, applications and publications in the relevant art to provide yet further embodiments. These and other changes can be made to the embodiments in light of the above-detailed description.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A handheld ultrasound probe, comprising:
an array of transducer elements configured to transmit an ultrasound signal toward a target structure in a region of interest;
an array of pulse generators, each of the pulse generators being coupled to a respective transducer element and including:
a driver circuit including an amplifier configured to receive a control signal and to output a driving signal,
a switching element having a control terminal coupled to an output of the amplifier of the driver circuit, the switching element including a gallium nitride field effect transistor (GaN FET), and
a resonant circuit coupled to the switching element and the respective transducer element, the resonant circuit being configured to provide a transmit pulse to the respective transducer element based on the driving signal.

2. The ultrasound probe of claim 1, further comprising a controller having a plurality of outputs, each of the plurality of outputs being coupled to a respective driver circuit, the controller being configured to generate the control signal.

3. The ultrasound probe of claim 2, wherein the controller comprises at least one of: an application-specific integrated circuit (ASIC) and a field programmable gate array (FPGA).

4. The ultrasound probe of claim 1, wherein the resonant circuit resonates at a natural resonance frequency of the respective transducer element.

5. An ultrasound pulse generation circuit, comprising:
a power supply;
a transducer element;
a driver circuit including an amplifier having a first input terminal and an output terminal, the amplifier being configured to receive a control signal at the first input terminal, and to provide a driving signal at the output terminal;
a switching element having a control terminal and a first conduction terminal, the control terminal being coupled to the output terminal of the amplifier of the driver circuit, the switching element including a gallium nitride field effect transistor (GaN FET); and
a resonant circuit coupled to the power supply at a first node, coupled to the first conduction terminal of the switching element at a second node, and coupled to the transducer element at a third node, the resonant circuit being configured to provide a transmit pulse to the transducer element based on the driving signal.

6. The ultrasound pulse generation circuit of claim 5, further comprising a controller coupled to the first input terminal of the amplifier, the controller being configured to generate the control signal.

7. The ultrasound pulse generation circuit of claim 6, wherein the controller comprises at least one of: an application-specific integrated circuit (ASIC) and a field programmable gate array (FPGA).

8. The ultrasound pulse generation circuit of claim 5, wherein the resonant circuit includes:
a first resistor having a first terminal and a second terminal, the first terminal coupled to the power supply at the first node;
an inductor having a first terminal coupled to the second terminal of the first resistor, and a second terminal coupled to the first conduction terminal of the switching element at the second node;
a second resistor having a first terminal coupled to the power supply at the first node, and a second terminal coupled to the second node; and
a capacitor having a first terminal coupled to the second node, and a first terminal coupled to the transducer element at the third node.

9. The ultrasound pulse generation circuit of claim 8, wherein the amplifier of the driver circuit includes a second input terminal coupled to an electrical ground.

10. The ultrasound pulse generation circuit of claim 8, wherein the switching element includes a second conduction terminal coupled to an electrical ground.

11. The ultrasound pulse generation circuit of claim 8, wherein the inductor has a value of inductance such that the resonant circuit resonates at a natural resonance frequency of the transducer element.

12. An ultrasound device, comprising:
a handheld ultrasound probe, including:
an array of transducer elements configured to transmit an ultrasound signal toward a target structure in a region of interest;
an array of pulse generators, each of the pulse generators being coupled to a respective transducer element and including:

a driver circuit including an amplifier configured to receive a control signal and to output a driving signal, a switching element coupled to an output of the amplifier of the driver circuit, and a resonant circuit coupled to the switching element and the respective transducer element, the resonant circuit being configured to provide a transmit pulse to the respective transducer element based on the driving signal; and a handheld computing device coupled to the ultrasound probe.

13. The ultrasound device of claim 12, wherein the handheld ultrasound probe further includes a power supply positioned within the handheld ultrasound probe, each of the pulse generators being coupled to the power supply.

14. The ultrasound device of claim 12, wherein the resonant circuit resonates at a natural resonance frequency of the respective transducer element.

15. The ultrasound device of claim 12, wherein the handheld computing device includes processing circuitry operably coupled to a controller circuit that provides the control signal to the driver circuit of each pulse generator.

16. The ultrasound device of claim 15, wherein the handheld computing device further includes a power supply coupled to the processing circuitry and to the pulse generators in the handheld ultrasound probe.

17. An ultrasound pulse generation circuit, comprising:
a power supply;
a transducer element;
a driver circuit having a first input terminal and an output terminal, the driver circuit being configured to receive a control signal at the first input terminal, and to provide a driving signal at the output terminal;
a switching element having a control terminal and a first conduction terminal, the control terminal being coupled to the output terminal of the driver circuit, the switching element including a gallium nitride field effect transistor (GaN FET); and
a resonant circuit coupled to the power supply at a first node, coupled to the first conduction terminal of the switching element at a second node, and coupled to the transducer element at a third node, the resonant circuit being configured to provide a transmit pulse to the transducer element based on the driving signal, the resonant circuit including:
a first resistor having a first terminal and a second terminal, the first terminal coupled to the power supply at the first node;
an inductor having a first terminal coupled to the second terminal of the first resistor, and a second terminal coupled to the first conduction terminal of the switching element at the second node;
a second resistor having a first terminal coupled to the power supply at the first node, and a second terminal coupled to the second node; and
a capacitor having a first terminal coupled to the second node, and a first terminal coupled to the transducer element at the third node.

18. The ultrasound pulse generation circuit of claim 17, wherein the driver circuit includes a second input terminal coupled to an electrical ground.

19. The ultrasound pulse generation circuit of claim 17, wherein the switching element includes a second conduction terminal coupled to an electrical ground.

20. The ultrasound pulse generation circuit of claim 17, further comprising a controller coupled to the first input terminal of the driver circuit, the controller being configured to generate the control signal.

* * * * *